United States Patent [19]

Erby et al.

[11] 3,992,415

[45] *Nov. 16, 1976

[54] METHOD OF PREPARING HALOGENATED LACTONE

[75] Inventors: William A. Erby, Alburtis; Robert A. Walde, Emmaus, both of Pa.

[73] Assignee: Air Products and Chemicals, Inc., Allentown, Pa.

[ * ] Notice: The portion of the term of this patent subsequent to Jan. 21, 1992, has been disclaimed.

[22] Filed: Aug. 19, 1974

[21] Appl. No.: 498,808

Related U.S. Application Data

[63] Continuation of Ser. No. 284,815, Aug. 30, 1972, Pat. No. 3,862,220, which is a continuation of Ser. No. 714,761, March 21, 1968, abandoned, which is a continuation-in-part of Ser. No. 541,096, April 8, 1966, Pat. No. 3,577,546.

[52] U.S. Cl. ............................................. 260/343.6
[51] Int. Cl.$^2$........................................ C07D 309/32
[58] Field of Search ..................... 260/343.6, 539 R

[56] References Cited
UNITED STATES PATENTS

3,275,505   9/1966   Herschler............................ 260/539
3,862,220   1/1975   Erby et al. ...................... 260/539 R Primary Examiner—Jane S. Myers
Attorney, Agent, or Firm—Leroy Whitaker; Everet F. Smith

[57] ABSTRACT

Direct halogenation of $C_4$–$C_{10}$ saturated keto monocarboxy acids or their acidogenic derivatives with elemental halogen to yield olefinic halogenated compounds (e.g. acids and lactones) containing at least four halogen atoms per molecule is disclosed. The halogenation is purely thermal with preferred temperature ranges being selected as a function of the particular end product desired. Halogenated products of the process as well as ammonia and amine salts of the acids made by the process are useful as insecticides, plant growth control agents and defoliants. Particularly useful products are those olefinic polychlorinated derivatives of gamma-keto-pentanoic acid which contain at least four chlorine atoms per molecule such as, for example, 2,3,5,5,5-pentachloro-4-keto pentenoic acid, its ammonium salt and its amine salts.

2 Claims, No Drawings

METHOD OF PREPARING HALOGENATED LACTONE

CROSS REFERENCE TO RELATED APPLICATION

This application is a continuation of application Ser. No. 284,815, filed Aug. 30, 1972, now U.S. Pat. No. 3,862,220, which in turn is a continuation of then co-pending application Ser. No. 714,761, filed Mar. 21, 1968, now abandoned, which in turn is a continuation in part of our prior copending application Ser. No. 541,096, filed Apr. 8, 1966, now U.S. Pat. No. 3,577,546, entitled "Preparation and Use of Polychloro Keto-Alkenoic Acids" which discloses and claims, inter alia, the use of compounds made by the method of the instant invention as pesticides, physiologically active materials and plant growth control agents. It is also related to our prior co-pending application Ser. No. 654,989 filed July 21, 1967, now U.S. Pat. No. 3,619,164 entitled "Method of Controlling Growth of Woody Jungle Plants" which discloses and claims the use of compositions comprising 2,3,5,5,5-pentachloro-4-keto pentenoic acid, which can be made by the method of the instant invention, for jungle defoliation.

BACKGROUND OF THE INVENTION

1. Field of the Invention

The present invention is concerned with novel methods for the synthesis of polyhalogenated and perhalogenated keto alkenoic acids, such as, for example, $C_4$ to $C_{10}$ mono-carboxylic acids, from the corresponding saturated keto acids, their esters, amides, anhydrides, lactones, acyl halides, and other acidogenic derivatives. More particularly, it pertains to methods of directly chlorinating and/or brominating gamma-keto-pentanoic acids and their derivatives to obtain acyclic and cyclic olefinic products which contain at least 4 halogen atoms per molecule.

2. Description of the Prior Art

While various investigators have reported the chlorination of gamma-keto $C_4$ to $C_{10}$ acids to the mono or dichloro stage, there is no report to date of any direct combined chlorination and dehydrogenation of such acids (or their acidogenic derivatives) to the unsaturated polyhalogenated or perhalogenated stage. As used herein, the terms "polyhalogenated" and "polychlorinated" refer, respectively, to compounds containing at least four halogen atoms per molecule (which may be of the same or of different halogens) and to compounds which contain at least four chlorine atoms per molecule. The terms "perhalogenated" and "perchlorinated" refer, respectively, to compounds in which all of the hydrogen atoms attached to carbon atoms in the molecule are substituted with haloglen atoms (which may be of the same or different halogens), and to compounds in which all of the hydrogen atoms attached to carbon atoms are substituted with chlorine atoms. The term "halogen" is intended to include chlorine, bromine or mixtures thereof.

A common gamma-keto-pentanoic acid, which is available in commerce, is levulinic acid. Early attempts to chlorinate levulinic acid directly resulted only in the production of mono- and dichloro derivatives. [Seissl, Annallen, 249, 288–303 (1888).] A number of polychloro-pentenoyl ketones, acids, acid halides and anhydrides have since been prepared by methods other than by the direct chlorination of levulinic acid [Zincke, Berichte der Deutsche Chemische Gessellschaft, 23, 240, (1890); 24, 916, (1891); 25, 2221, (1892); 26, 506, (1893); and 26, 317 (1893)]

U.S. Pat. No. 3,275,505 does disclose the direct halogenation of levulinic acid. However, the reaction temperatures are between 100° and 125° C and, even with high degrees of halogenation, no more than four atoms of halogen are added per molecule of levulinic acid. Further, there is no conversion of the acid from a saturated to an olefinic compound.

BRIEF SUMMARY OF THE INVENTION

Briefly summarized, the invention pertains to the halogenation, particularly with chlorine, of saturated keto mono carboxylic acids of which levulinic acid is a prime example. It also relates to subsequent esterification and salt formation. While the invention may be utilized in connection with either chlorine or bromine or both, those compounds produced from chlorine and/or bromine and levulinic acid are possessed of particular utility in connection with growth control of plants and in insecticidal applications. One particular compound, which can be made by processes of the invention, and which is designated as 2,3,5,5,5-pentachloro-4-keto pentenoic acid has a unique capacity for wilting the foliage of woody jungle plants such as cotton. This characteristic is the basis for a novel method of harvesting cotton which is described in U.S. Pat. No. 3,472,004 entitled "Method of Harvesting Cotton" of which we are among the inventors. Further, chlorinated compounds of the invention are of value as jungle defoliants. Other uses of the compounds made by the instant process are described in the parent application referred to above.

In most general terms, the invention contemplates the direct chlorination and/or bromination of saturated keto mono carboxylic acids or their acidogenic derivatives (e.g. esters, amides, etc.) over relatively long periods of time and at elevated temperatures. Since the reactions are exothermic, it is usually preferred to halogenate at rates which prevent violent fluctuations of temperature such as would cause product degradation or undue increase in by-product formation. When batch processes are used, it is preferred to raise reaction temperatures gradually as the reaction proceeds over a period of time to the optimum limits.

Conditions utilized are always severe enough to cause both dehydrogenation and the addition of at least four halogen atoms per molecule of acid. Under more severe conditions, additional halogen may be incorporated to reach the perhalogenated state, and further, to cause formation of cyclic compounds.

The reactions can best be illustrated with respect to the chlorination of levulinic acid and the summary discussion which follows is generally related to the examples in the discussion of the preferred embodiments below. These embodiments utilize levulinic acid or acidogenic derivatives thereof.

In the instant process, the acid or acidogenic material is reacted with gaseous chlorine while the temperature is gradually increased from ambient to a maximum final temperature of 270° C. Where the starting material is levulinic acid and the reaction is terminated at 170° to 190° C, the final product will be preponderantly a tetrachloro-4-keto-pentenoic acid. Where the reaction is terminated between 190° and 210° C the reaction product is a pentachloro-4-keto pentenoic acid. Where the reaction is terminated at a final temperature of 212° to 260° C, the final product is a hexachloro-2-pentenoic acid-4-lactone. It has been found that, where it is desired to produce an end product which is substantially pure 2,3,5,5,-pentachloro-4-keto-pentenoic acid, the most effective technique for obtaining a pure product is to terminate the reaction at temperatures above 212° C, to produce the corresponding lactone and to, thereafter, utilize acid hydrolysis, preferably in the presence of chlorine gas, to convert the lactone to the desired acid. Reaction times are on the order of 90 hours.

The above reactions may be conducted with bromine instead of chlorine. Further, a reaction may be begun with one type of halogen, discontinued before perhalogenation is completed, and reacted with yet another halogen to the completion of halogenation so that a given molecule will contain atoms of different halogens.

The halogenated compounds produced by the novel method of the present invention from 5 carbon keto carboxy acids correspond, in form of the carboxylic acids or their esters, to the formula.

wherein $x$ is 0 or 1, and R is H or the residue of an esterifying organic hydroxy compound such as an alcohol or phenol.

Compounds corresponding to the above formula are produced in high yields and exceptional purity in accordance with the invention by direct chlorination of levulinic acid or its acidogenic derivatives under controlled conditions of time and temperature to obtain an olefinic linkage at the carbon in the position alpha to the carboxy group. Illustrative of the compounds thus obtained and certain derivatives (e.g. esters and salts thereof) are:

1)
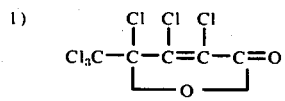

2,3,4,5,5,5-hexachloro-2-pentenoyl-4-lactone (perchloro angelica lactone)

2)
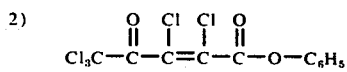

phenyl-2,3,5,5,5-pentachloro-4-keto-2-pentenoate

3)
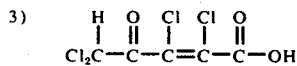

2,3,5,5-tetrachloro-4-keto-2-pentenoic acid

4)
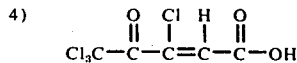

3,5,5,5-tetrachloro-4-keto-2-pentenoic acid

5)
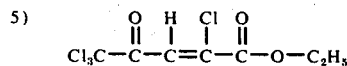

ethyl 2,5,5,5-tetrachloro-4-keto-2-pentenoate

6)
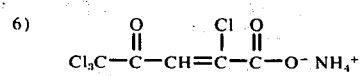

ammonium salt of 2,5,5,5-tetrachloro-4-keto-2-pentenoic acid

7)
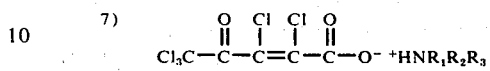

wherein $R_1$ is alkyl and $R_2$ and $R_3$ are each alkyl or hydrogen, these compounds being amine salts of 2,3,5,5,5-pentachloro-4-keto-2-pentenoic acid The polychloro-compounds so produced have been found to have pronounced activity as insecticides, herbicides and cotton defoliants, such that, in a process based upon low cost levulinic acid and chlorine, commercially valuable biologically active chemicals can be produced at low cost.

Esterification of the free acid can be effected with monohydric or polyhydric alcohol. Thus, by reacting compound (1) with pentaerythritol, a mixture comprising mono-and di-esters may be obtained.

Ammonium and amine salts of the free acids can also be formed by reacting the same, respectively, with ammonia or primary, secondary or tertiary alkyl amines including, for example, dipropyl amine, isopropyl amine, N,N-dimethyl hexadecylamine, N-N-dimethyl octadecylamine, N-N-dimethyl dodecylamine and cocoamine.

Accordingly, it is an object of the invention to provide a method whereby direct halogenation of $C_4$ to $C_{10}$ saturated keto mono carboxy acids or their acidogenic derivatives at changing temperatures may be utilized to effect both halogenation and dehydrogenation.

It is a further object of the invention to provide a direct method of halogenation where, selectively, dependent upon the reaction conditions utilized and the reactants present, one may obtain acyclic halogenated olefinic keto acids or related cyclic compounds both of which are capable of further reactions such as esterification.

It is additionally an object of the invention to provide processes for the direct thermal chlorination of keto carboxy acids.

These and other objects of the invention will be apparent to those skilled in the art from a consideration of the exemplary description which follows.

It should be appreciated that neither the abstract of the disclosure nor the summary of the invention above is intended to constitute a limitation on its extent. They are inserted merely as aids in information retrieval and, therefore, the true scope of the invention is to be determined only by a reasonable interpretation of the appended claims in light of the disclosure herein contained.

DESCRIPTION OF PREFERRED EMBODIMENTS

The desired compounds are produced, in accordance with the invention, for example, by passing chlorine into levulinic acid or into an acidogenic derivative of levulinic acid over an extended period of time while raising the temperature gradually from ambient temperature to an ultimate temperature in the region of 150° to 270° C. As halogen is added, the activation energy for subsequent substitutions increases. Therefore, it is necessary to increase the temperature as the reaction proceeds although, in equivalent continuous processes, cold feed can be added to large agitated bodies of liquid maintained at optimum temperature and such fresh feed is, in effect, gradually raised in temperature.

Premature elevation of temperature can induce decomposition and polymerization of unsuitable intermediates. However, the thermal stability of the intermediates increases as the halogen content increases, which allows the reaction temperature to be safely increased as halogenation proceeds. Since the reactions are exothermic, once they have been initiated, it is important to control the rate of addition of halogen so that temperatures will not rise above the capacity for thermal stability of the system in its then current degree of halogenation. Briefly, then, the rate of addition of halogen is a function of temperature in practicing the invention.

There are thus obtained in high yield and good purity, polychloro and perchloro keto- pentenoic acids and their derivatives, having four or more chlorine atoms per molecule. The acids obtained can be readily converted to the corresponding salts, esters and amides by methods generally known in the art.

The distinct properties of the compounds obtained by the practice of the invention which render them useful, and effective as insecticidal and herbicidal compositions, are believed to reside in the simultaneous presence in the carboxylic compound of the polychloro function combined with the effect of the olefinic linkage, and the keto type structure. Despite the high insecticidal activity displayed by these compounds, they are highly selective in their action on plants, whereby they also have utility as plant growth control and defoliating agents.

The following examples illustrate the purely thermal embodiments of the invention but are not intended to limit the same.

EXAMPLE 1

Chlorine gas was passed continuously through 588 g. of ethyl levulinate with rapid mixing. The temperature rose exothermally to 60° and remained there for 26 hours. When the temperature started to fall, heat was applied to raise the temperature to 112° C. The temperature of the reaction was then allowed to rise slowly, with further chlorination, to 180° C, and kept there for 35 hours. More heat was applied and the temperature was further increased to 212° C and held at that temperature for 14 hours. The total reaction time thus was 75 hours. At the end of this period, the chlorine content of the product was 70.5% and 1435 grams of material were recovered. Gas chromatographic, infra-red spectographic, ultimate analysis and other physical tests showed 93% of the product to consist of the 2,3,4,5,5,5-hexa-chloro-2-pentenoyl-4-lactone, (i.e. perchloro-angelica lactone) having the following formula:

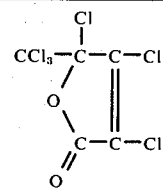

| | Found | Theory |
|---|---|---|
| Boiling Point | 74.5° C/0.2 mm Hg | |
| Refractive Index, 20°/D | 1.5465 | |
| Density, g/ml at 20° C | 1.6357 | |
| Chlorine Content | 70.2% | 69.8% |
| Carbon Content | 20.2% | 19.8% |
| Molecular Weight | 315 | 305 |

Strong characterizing adsorption peaks for infra-red were at 1835 cm$^{-1}$ and 974 cm$^{-1}$. Weight recovery on the basis of this structure was 94% of theoretical.

Halogenated angelica lactone behaves, in various chemical reactions, as if it were an acyl halide of the type:

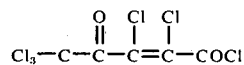

Thus, it was readily esterified by reaction with sodium phenoxide to yield a phenyl ester of pentachloro-4-keto-2-pentenoic acid.

EXAMPLE 2

11.6 lb. of levulinic acid were placed in a vessel with a sintered glass sparger which allowed rapid and uniform dispersion of elemental halogen through the contents. Chlorine was passed rapidly into this system, with the initial temperature maintained below 90° C by external cooling. After 24 hours of chlorination, hydrogen chloride evolution decreased noticeably. The temperature was then raised to 125° C for 24 hours while an excess of chlorine was maintained in the reaction system (as evidenced by the presence of free chlorine in the reactor exit gas and yellow color in the reactor solution). The temperature was then slowly increased to 170° C and maintained at that temperature for over 8 hours, with continuous chlorine additional until HCl evolution again diminished. The reaction product crystallized on cooling.

A sample of this product, after recrystallization, was a white solid having a melting point of 117°–118° C. While the reaction product might have been expected to be a broad mixture of trichloro to hexachloro-compounds with numerous stereo-isomers, the product was, surprisingly, predominantly the unsaturated tetrachloro-keto-acid with very little trichloro or pentachloro acid present.

EXAMPLE 3

Using essentially the same equipment as in Example 2, levulinic acid was chlorinated directly by the introduction of chlorine. The initial reaction temperature held at 60° to 90° C until about one-third of the total chlorine had been introduced and reacted. After the initial one-third had reacted, the reaction temperature was allowed to increase slowly, by the exothermic heat of chlorination, to the vicinity of 170° C and, by supplementary heating, to 190° to 200° C while maintaining a substantial excess of chlorine. The reaction mixture was held in the temperature range of 190° to 200° C until there was a substantial drop in the rate of chlorine absorption and HCl release. At this point, a sample withdrawn from the reactor and washed with n-heptane gave a white crystalline product found, on ultimate analysis, to be principally $C_5Cl_5HO_3$. Analytical results were as follows:

|  | Theoretical | Found |
|---|---|---|
| Carbon, % | 20.98 | 21.25 |
| Hydrogen, % | 0.35 | 0.38 |
| Chlorine, % | 61.92 | 61.17 |
| Mol. Wt. | 286 | 275 |
| Melt. Pt., ° C | — | 83–85 |
| Neutralization Equiv. | 286 | 278 |

Infra-red analysis showed the following characteristic peaks:

| | |
|---|---|
| $-\overset{\overset{O}{\|\|}}{C}-$ | 1785 cm$^{-1}$ |
| $-C=C-$ (conj.) | 1625 cm$^{-1}$ |
| $-\overset{\overset{O}{\|\|}}{C}-OH$ | 1815 cm$^{-1}$ |
| $-OH$ | 3375 cm$^{-1}$ |
| $-Cl$ | 740 cm$^{-1}$ | from which the structural formula was indicated to be:

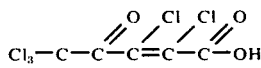

2,3,5,5,5-pentachloro-4-keto-2-pentenoic acid

EXAMPLE 3-A

Cis-configuration of this structure was confirmed by production of the same unsaturated polychloro-compound by the acid hydrolysis of the related hexachloro-angelica-lactone of Example 1.

EXAMPLE 4

To further point up the criticality of temperature in direct chlorination by the present process, the reaction product of Example 3, principally the pentachloro-4-keto-pentenoic acid, was then heated from 200° C to about 260° C with the continuous addition of chlorine. After 24 hours, at 250° to 260° C, the reaction product was practically completely converted to the liquid unsaturated hexachloro-lactone of Example 1.

EXAMPLE 5

Levulinic acid (11.6 lbs.) was placed in a reactor equipped with a gas dispersion tube, a stirrer and a heating-cooling mechanism. Chlorine (26 lbs/hr) was then passed through the dispersion tube into the rapidly stirred mixture. An exothermic reaction occurred, and the temperature was allowed to increase to 100° C. It was maintained at this temperature by proper adjustment of the cooling bath. The reaction was allowed to continue until a decrease in the reaction exotherm was indicated by a drop in the temperature inside the reactor.

On completion of this phase of the reaction, the temperature was slowly raised to 130°–140° C by increasing the temperature of the bath. Care was taken during this operation to prevent darkening of the reaction mixture caused by raising the temperature too rapidly. Again an exotherm was noted. The chlorine flow rate during the rest of the reaction was maintained fast enough to insure that a small amount of chlorine was in the reactor exit gas. The reactor was held at this temperature until the heat output of the reaction again decreased.

Upon completion of the second phase, the temperature was again raised to 250° C. The reaction was then maintained at this temperature until completion of the reaction. This was confirmed by infra-red analysis of the sample. The spectrum contained no absorption peak between 2.5 and 3.5 microns. A very sharp carbonyl absorption band of high intensity appeared at 5.45 microns. This was accompanied by a small shoulder at 5.55 microns. An unsaturation absorption band was also evident at 6.15 microns.

The reaction product was thus shown to be predominantly 2,3,4,5,5,5,hexachloro-2-pentenoyl-4-lactone.

EXAMPLE 6

The reaction product of Example 5 was converted quantitatively to 2,3,5,5,5-pentachloro-4-keto pentenoic acid using the following hydrolysis technique.

The reaction product was adjusted in temperature to 100° C and 3.48 lbs. of water added (i.e. 30% of the levulinic acid charge). The reaction mixture was then rapidly stirred while a slow stream of chlorine was passed through the system while the temperature was maintained at 100° C.

When this hydrolysis was complete, the carbonyl region of the infra-red spectrum of the product showed two bands, one at 5.5 and one at 5.6 microns. A broad acid-OH absorption band appeared at 3 microns. The temperature was then allowed to drop to approximately 90°. Water was added until phase separation occurred. The water in the upper layer was then siphoned out as completely as possible. The product was washed two more times with water and dried.

The total yield of product under these conditions, was in the neighborhood of 80%. The remainder of the material was presumed lost by entrainment in the exit gases at the high temperature, or by break-down to dichloromaleic anhydride. The dichloromaleic anhydride formation could account for about 10% of the lost product.

Direct chlorination of levulinic acid readily forms the simple chloro-derivative. The reaction has been shown by others to proceed with increasing difficulty only to the tetrachloro stage. Surprisingly, we have found that on extended chlorination at 170° to 270° C, preferably below 250° C, in the presence of an excess of chlorine, that four or more hydrogen atoms are substituted by chlorine atoms and two hydrogen atoms are simultaneously split off (as HCl) to produce a new species of olefinically unsaturated derivatives. The products of chlorination according to the invention are fully olefinically unsaturated at the tetra-, penta- and hexachloro levels. Unless temperature is carefully controlled, particularly during the early stages of halogenation, one obtains only polymeric products of a tarry nature.

The process of producing unsaturated polychloro-4-keto-pentenoic acid or its acidogenic derivatives, with at least four chlorine atoms per molecule, has been exemplified above starting with levulinic acid or its ester. However, the process is not limited to these starting materials alone. Acyl halides, anhydrides and lactones of levulinic acid can be used, and, since chlorination of levulinic acid and its acidogenic derivatives to monochloro- and dichloro-state has been effected heretofore, such intermediately chlorinated derivatives can be used as well, whether chlorine is in the alkyl chain, in the acyl group, or in both. Homologous keto acids and keto acids relatable to levulinic acid which contain the structure:

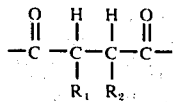

wherein $R_1$ and $R_2$ are independently selected from the group consisting of hydrogen, halogen and lower alkyl are similarly polychlorinatable or perchlorinatable according to the invention.

While the invention is principally concerned with chlorination, it will be understood that other halogenation reactions, such as bromination, can also be effected by stepwise temperature elevation during halogenation to obtain corresponding unsaturated keto acids having four or more bromine substituents.

Other examples of similar reactions utilizing chlorine, bromine or both are presented below in tabular form. The techniques utilized were generally similar to those described in Example 5.

shorter time, though with probably less selectivity, at moderately higher temperatures.

After the reactions described above, the reaction products may be further reacted to produce esters, amides and salts. When salts are desired of those products which are lactones, it is first necessary to obtain the free acid form by hydrolysis. The following are illustrative examples of salt formation:

EXAMPLE S-1

The product of Example 3 was dissolved in ether (other suitable solvents include, for example, toluene) and ammonia was slowly bubbled through the solution. An excess of acid was maintained in the media in order to increase yield. The ammonium salt of 2,3,5,5,5-pentachloro-4-keto-2-pentenoic acid was obtained. A portion of the product was further purified by recrystallization from ethyl acetate.

EXAMPLE S-2

The product of Example 3-A, subsequent to the hydrolysis step, was subjected to the method of Example S-1 and the same ammonium salt was obtained as from Example S-1.

Salts of the various halogenated keto acids of the invention are obtained by reacting them (in their acid form) with ammonia or organic amines, preferably those containing from 1 to 18 carbons. As used henceforth herein, the term "organic amines" is intended to encompass such compounds as well as amines which have been reacted with an alkylene oxide. Amines

| Example No. | Starting Acid | Halogen | Max. Tem. | Total Time | Product |
|---|---|---|---|---|---|
| 7 | Levulinic | Br$_2$ | 175° C | 16 | 2,3,5,5,-tetrabromo-4-ketopentenoic acid |
| 8 | Levulinic | Br$_2$ | 200° C | 16 | 2,3,5,5,5-pentabromo-4-keto-pentenoic acid |
| 9 | Levulinic | Br$_2$ | 250° C | 80 | 2,3,4,5,5,5-hexabromo-2-pentenoyl-4-lactone |
| 10 | Levulinic | Br$_2$ then Cl$_2$ | 200° C | 16 | 2,5,5 trichloro-3,5-dibromo-4-ketopentenoic acid |
| 11 | 4-keto-hexanoic acid | Cl$_2$ | 220° C | 30 | 2,3,4,5,5,6,6-heptachloro hexenoyl-4-lactone |
| 12 | 5-methyl-4-oxo-hexanoic acid | Cl$_2$ | 215° C | 30 | 2,3,4,5,6,6-hexachloro-5-trichloromethyl-4-hexenonyl lactone |
| 13 | 6-hydroxy-6,6-di-trifluoromethyl-4-keto hexanoic acid | Cl$_2$ | 180° C | 40 | 2,3,5,5,6-hexachloro-6,6-di-trifluoromethyl-4-keto hexenoic acid |
| 14 | 6,6-dimethyl-4-keto heptanoic acid | Cl$_2$ | 200° C | 30 | 2,3,4,5,5,-pentachloro-6,6-dimethyl-4-heptanoyl lactone |
| 15 | 5,5,6-trimethyl-4-keto heptanoic acid | Cl$_2$ | 225° C | 35 | 2,3,4,5 tetrachloro 5,6,6-trimethyl-4-heptanonyl lactone |
| 16 | 4-ketohexanoic acid | Br$_2$ | 230° C | 40 | 2,3,4,5,5,6,6-octabromo hexanoyl-4-lactone |
| 17 | 6,6-dimethyl-4-keto heptanoic acid | Br$_2$ | 230° C | 40 | 2,3,4,5,5,6-hexabromo-6,6-dimethyl heptanoyl-4-lactone |

Definite temperature limits have been shown for each halogenation step. However, it will be appreciated by those conversant with the art that reasonable variations can be made in the prescribed temperature and time of halogenation by which the rate and extent of halogenation and dehydrogenation can be varied in any step of the process. For instance, whereas chlorination and dehydrogenation of ethyl levulinate was affected over periods as long as 72 hours with rising temperature and with a significant quotient of reaction time at or above 210° C., a similar degree of chlorination and dehydrogenation might be effected in somewhat which have been utilized in this connection include n-octylamine, N-oleyl-1,3-propylene diamine, ethylamine, diethyl amine, triethylamine, propylamine, dipropyl amine, isopropyl amine, ethanol amine, diisopropyl amine, butyl amine, dibutyl amine, hexyl amine, 2-Ethylhexyl amine, N-methylbutyl amine, etc.

One of the utilities of the compounds of the process is exemplified by data obtained using the product of Example 1 as the active ingredient. Herbicidal characteristics were determined by spraying the active material at a rate of 2 lbs./acre using a water suspendable oil formulation thereof. In the table results are reported on a linear numerical scale where 0 indicates no effect and 10 indicates a complete kill.

| A. Weeds | |
|---|---|
| Pigweed | 10 |
| Johnsongrass | 9 |
| Setaria | 8 |
| B. Crops | |
| Corn | 6 |
| Oats | 2 |
| Wheat | 1 |

Another utility possessed by compounds which can be made using the processes of the instant invention arises in connection with the wilt-harvesting of cotton. Application of these materials to cotton prior to harvesting causes wilting of foliage to occur in a short time and promotes boll opening. By harvesting cotton when the plant is wilted yield and quality of cotton are improved. Further, thereafter, defoliation occurs and the balance of the cotton can be harvested. All of these agricultural techniques are discussed at length in U.S. Pat. No. 3,473,004 referred to above. Suffice it to say at this point, that it is commercially desirable for the compounds under consideration to wilt and/or defoliate cotton plants. Some test data demonstrative of this ability is given below in a series of tests performed with the compound of Example 3 and various of its salts. Applications of the indicated compound at the rate of active ingredient shown was in the form of a water extendible concentrate which was diluted to a spray volume equivalent to 20 gallons per acre.

| Compound of | Rate (lbs./acre) | % Wilt 24 hrs. | % Wilt 48 hrs. | % Defoliation 5 days | % Defoliation 13 days |
|---|---|---|---|---|---|
| 1 Example 3 | 4 | 80 | 80 | 50 | 50 |
| 2 Ammonium salt | 4 | 80 | 90 | 95 | 95 |
| 3 Monomethyl amine | 4 | 40 | 40 | 25 | 35 |
| 4 Monethyl amine salt | 4 | 50 | 55 | 30 | 30 |
| 5 Monoisopropyl amine salt | 4 | 55 | 70 | 20 | 20 |
| 6 Triethylamine salt | 4 | 40 | 50 | 5 | 5 |
| 7 Monoethanolamine salt | 4 | 40 | 40 | 25 | 25 |
| 8 Triethanolamine salt | 4 | 20 | 20 | 2 | 2 |

It has thus been demonstrated how methods of the invention achieve the objects initially stated and produce compounds having various agricultural utility.

Obviously, many modifications and variations of the invention, as hereinbefore set forth, may be made without departing from the spirit and scope thereof. Therefore, only such limitations should be imposed as are indicated in the appended claims.

We claim:
1. A method for producing 2,3,4,5,5,5-hexachloro-2-pentenoyl-4-lactone which comprises treating levulinic acid or an ester thereof with elemental chlorine initially at substantially ambient temperature and raising the temperature to about 212° C. and continuing the chlorination in the range of about 212° to about 260° C. until cyclization occurs and sufficient chlorine has been added to yield the desired product.
2. The method of claim 1 wherein the starting material is ethyl levulinate.

* * * * *